US010617383B2

United States Patent
Masumoto (10) Patent No.: US 10,617,383 B2
(45) Date of Patent: Apr. 14, 2020

(54) MEDICAL IMAGE DISPLAY APPARATUS, METHOD, AND MEDIUM

(71) Applicant: FUJIFILM Corporation, Tokyo (JP)

(72) Inventor: Jun Masumoto, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 1434 days.

(21) Appl. No.: 14/656,068

(22) Filed: Mar. 12, 2015

(65) Prior Publication Data

US 2015/0257730 A1 Sep. 17, 2015

(30) Foreign Application Priority Data

Mar. 17, 2014 (JP) ................. 2014-052887

(51) Int. Cl.
| | |
|---|---|
| *A61B 6/00* | (2006.01) |
| *A61B 8/08* | (2006.01) |
| *A61B 8/00* | (2006.01) |
| *G06T 19/00* | (2011.01) |

(Continued)

(52) U.S. Cl.
CPC .......... *A61B 8/0841* (2013.01); *A61B 6/5247* (2013.01); *A61B 8/0833* (2013.01); *A61B 8/463* (2013.01); *A61B 8/466* (2013.01); *A61B 8/5261* (2013.01); *G06T 19/00* (2013.01); *A61B 6/5223* (2013.01); *A61B 8/4254* (2013.01); *A61B 2017/3413* (2013.01); *A61B 2034/107* (2016.02); *G06T 2210/41* (2013.01); *G06T 2219/008* (2013.01)

(58) Field of Classification Search
CPC .................................. A61B 8/0841
See application file for complete search history.

(56) References Cited

U.S. PATENT DOCUMENTS

| | | | | |
|---|---|---|---|---|
| 6,336,899 B1 * | 1/2002 | Yamazaki | ........... | A61B 8/0833 128/916 |
| 2010/0240997 A1 * | 9/2010 | Ichioka | .................... | A61B 8/00 600/443 |

(Continued)

FOREIGN PATENT DOCUMENTS

| | | |
|---|---|---|
| JP | 2002-112998 A | 4/2002 |
| JP | 2012-040220 A | 3/2012 |

OTHER PUBLICATIONS

Communication dated Aug. 21, 2015 from the European Patent Office in counterpart application No. 15158943.9.

*Primary Examiner* — Rochelle D Turchen (74) *Attorney, Agent, or Firm* — Sughrue Mion, PLLC (57) ABSTRACT

Scanning a subject with an ultrasonic probe and obtaining an ultrasonic image of the subject. Obtaining a cross-sectional image of a cross-section of a three-dimensional image corresponding to the ultrasonic image from the three-dimensional image, the three-dimensional image including a puncture line set for a puncture needle and a superimposed columnar index having a central axis line on the puncture line and opacity which is reduced with the distance from the central axis line. Displaying the ultrasonic image and the cross-sectional image. In this case, the thickness, opacity, and cross-sectional shape of the index displayed on the cross-sectional image vary according to the positional relationship between the scan plane of the ultrasonic probe and the cross-section in which the puncture line is set.

14 Claims, 6 Drawing Sheets

(51) Int. Cl.
    *A61B 17/34*    (2006.01)
    *A61B 34/10*    (2016.01)

(56) References Cited

U.S. PATENT DOCUMENTS

2010/0298704 A1* 11/2010 Pelissier .............. A61B 8/0833
                                                       600/443
2011/0216958 A1*  9/2011 Satoh ........................ G06T 7/33
                                                       382/131
2012/0078103 A1*  3/2012 Tashiro ................ A61B 8/0841
                                                       600/443

* cited by examiner

MEDICAL IMAGE DISPLAY APPARATUS, METHOD, AND MEDIUM

CROSS-REFERENCE TO RELATED APPLICATIONS

The present application claims priority under 35 U.S.C. § 119 to Japanese Patent Application No 2014-052887 filed on Mar. 17, 2014. The above application is hereby expressly incorporated by reference, in its entirety, into the present application.

BACKGROUND OF THE INVENTION

Field of the Invention

The present invention relates to a medical image display apparatus, method, and program capable of supporting an operation of an ultrasonic probe in an ultrasonic diagnostic system that obtains an ultrasonic image of a subject.

Description of the Related Art

Heretofore, ultrasonic diagnostic systems using ultrasonic images have been put into practical use in medicine. Generally, such type of an ultrasonic diagnostic system includes an ultrasonic probe and a main body connected to the ultrasonic probe, and generates an ultrasonic image by transmitting an ultrasonic wave from the ultrasonic probe toward a subject to scan the subject, receiving an ultrasonic echo by the ultrasonic probe, and electrically processing the received echo signal in the main body.

Further, an ultrasonic diagnostic system provided with a structure that allows a puncture needle to be attached to the ultrasonic probe (puncture adapter) to facilitate a biopsy of a specific measuring target region of a subject using a dedicated puncture needle is also known. Such a system may display a guide line representing an approach path when the puncture needle is punctured (hereinafter, puncture guide line) on a display. When the ultrasonic diagnostic system is activated while puncturing a puncture needle into a subject using such an ultrasonic probe following the guide line, the operator may confirm the image inside the subject and the movement of the puncture needle at the same time, whereby a puncture operation (e.g., biopsy, drainage, and the like) may be performed safely.

In the meantime, medical images other than ultrasonic images, such as X-ray CT images, MRI images, and the like are clearer that the ultrasonic images. Hence, a system that displays a real-time ultrasonic image together with a cross-sectional image of an X-ray CT image, a MRI image, or the like whose cross-section is the same as that of the ultrasonic image being displayed is proposed (refer to Japanese Unexamined Patent Publication No 2002-112998). Further, in such a system, by setting a line along which the puncture needle is to be punctured (hereinafter, puncture line) in the cross-sectional image based on a tumor or the like, moving the ultrasonic probe such that the scan plane of the ultrasonic probe and the cross-section that includes the puncture line (hereinafter, puncture cross-section), i.e., the ultrasonic image and the cross-sectional image, are aligned with each other, and performing a puncture at the aligned position, the puncture guide line of the puncture needle and the set puncture line may be aligned and the puncture may be performed safely. In this case, if the puncture guide line is displayed in the ultrasonic image, the scan plane of the ultrasonic probe and the puncture cross-section may be aligned by moving the ultrasonic probe such that the puncture guide line and the puncture line included in the cross-sectional image are aligned with each other.

But the operation of aligning the scan plane of the ultrasonic probe with the puncture cross-section is very complicated, because the position and the direction of the ultrasonic probe need to be changed many times on the body surface.

Consequently, a method is proposed in which two rectangular distance marks indicating the distance between the puncture line and the puncture guide line are disposed, one on the puncture guide line of the ultrasonic image and the other on the puncture line of the cross-sectional image, and the size of the rectangular distance mark is changed and displayed according to the distance between the scan plane of the ultrasonic probe and the puncture cross-section (refer to Japanese Unexamined Patent Publication No. 2012-040220). The use of the method described in Japanese Unexamined Patent Publication No. 2012-040220 may facilitate the operation of aligning the scan plane of the ultrasonic probe with the puncture cross-section by aligning the puncture guide line with the puncture line.

SUMMARY OF THE INVENTION

The method described in Japanese Unexamined Patent Publication No. 2012-040220, however, requires that changes in the size of the two distance marks need to be constantly confirmed, so that the sense of distance between the puncture guide line and the puncture line is difficult to understand intuitively.

The present invention has been developed in view of the circumstances described above, and it is an object of the present invention to facilitate the operation of aligning the scan plane of the ultrasonic probe with the cross-section that includes the puncture line.

A medical image display apparatus according to the present invention includes:

an ultrasonic image obtaining means that scans a subject with an ultrasonic probe and obtains an ultrasonic image of the subject;

a cross-sectional image obtaining means that obtains a cross-sectional image of a cross-section of a three-dimensional image corresponding to the ultrasonic image from the three-dimensional image, the three-dimensional image including a puncture line set for a puncture needle and a superimposed columnar index having a central axis line on the puncture line and opacity which is reduced with the distance from the central axis line; and a display control means that displays the cross-sectional image.

The term "a puncture line set for a puncture needle" refers to a line representing a path for approaching the puncture needle to a lesion portion from the body surface of the subject.

In the medical image display apparatus according to the present invention, the opacity of the index may be reduced linearly with the distance from the central axis line.

Further, in the medical image display apparatus according to the present invention, the opacity of the index may be reduced in a Gaussian distribution with the distance from the central axis line.

Still further, in the medical image display apparatus according to the present invention, the index may have different distance scales between a direction parallel to a puncture cross-section that includes the puncture line and a direction orthogonal to the puncture cross-section. The term "different distance scales" as used herein refers to that the distance from the central axis of the index to the outer edge differs between a direction parallel to a puncture cross-section that includes the puncture line and a direction orthogonal to the puncture cross-section. For example, the index may have different distance scales between a direction parallel to a puncture cross-section that includes the puncture line and a direction orthogonal to the puncture cross-section by forming the index in an elliptical shape in cross-section and superimposing the index such that the long axis of the ellipse is disposed in a direction parallel to a puncture cross-section that includes the puncture line while the short axis is disposed in a direction orthogonal to the puncture cross-section.

Further, in the medical image display apparatus according to the present invention, the index may have a circular cylindrical shape.

Still further, in the medical image display apparatus according to the present invention, the index may be written in the three-dimensional image.

Further, in the medical image display apparatus according to the present invention, the index may be generated separately from the three-dimensional image, and the cross-sectional image obtaining means may be a means that superimposes the index on the three-dimensional image and obtains the cross-sectional image.

Still further, in the medical image display apparatus according to the present invention, the display control means may be a means capable of switching between at least two of display, non-display, and translucent display of the index on the cross-sectional image.

Further, the medical image display apparatus according to the present invention may further includes a puncture line setting means that sets the puncture line in the three-dimensional image.

A medical image display method according to the present invention includes the steps of:

scanning a subject with an ultrasonic probe and obtaining an ultrasonic image of the subject;

obtaining a cross-sectional image of a cross-section of a three-dimensional image corresponding to the ultrasonic image from the three-dimensional image, the three-dimensional image including a puncture line set for a puncture needle and a superimposed columnar index having a central axis line on the puncture line and opacity which is reduced with the distance from the central axis line; and displaying the cross-sectional image.

Note that the medical image display method according to the present invention may be provided as a program to be executed by a computer.

According to the present invention, a columnar index having a central axis line on a puncture line and opacity which is reduced with the distance from the central axis line is superimposed on a three-dimensional image, and an ultrasonic image and a cross-sectional image of a cross-section of the three-dimensional image, superimposed with the index, corresponding to the ultrasonic image are displayed, Therefore, in case that the scan plane by the ultrasonic probe is away from the puncture line, the index appears thin and pale, and the index becomes thicker and an area adjacent to the center thereof becomes darker as the scan plane comes closer to the puncture line. Thus, the distance between the scan plane by the ultrasonic probe and the puncture cross-section may be intuitively recognized by the thickness and opacity of the index. Further, in case that the scan plane by the ultrasonic probe is inclined with respect to the puncture cross-section, a cross-section of the index appears, so that it may also be recognized easily that the scan plane by the ultrasonic probe is inclined with respect to the puncture cross-section. Therefore, the operation of aligning the scan plane by the ultrasonic probe with the puncture cross-section that includes the puncture line may be facilitated.

Further, by reducing the opacity of the index in a Gaussian distribution with the distance from the central axis line, it is easier to recognize that the scan plane by the ultrasonic probe comes closer to the puncture line.

Further, by making the index to have different distance scales between a direction parallel to the puncture cross-section and a direction orthogonal to the puncture cross-section, the difference in the amount of rotation and direction between the cross-section of the three-dimensional image that include the puncture line and the scan plane by the ultrasonic probe may be recognized as the difference in thickness of the index. Hence, the relationship in the amount of rotation and direction between the cross-section of the three-dimensional image in which the puncture lines is present and the scan plane by the ultrasonic probe may also be recognized intuitively.

In a case in which the index is generated separately from the three-dimensional image, by allowing at least two of display, non-display, and translucent display of the index on the cross-sectional image to be switched, the index may be hidden or displayed translucently so as not to hindering when puncturing, so that the position of the puncture target in the cross-sectional image may be confirmed accurately.

DETAILED DESCRIPTION OF THE PREFERRED EMBODIMENTS

Hereinafter, embodiments of the present invention will be described with reference to the accompanying drawings.

Figure 1:
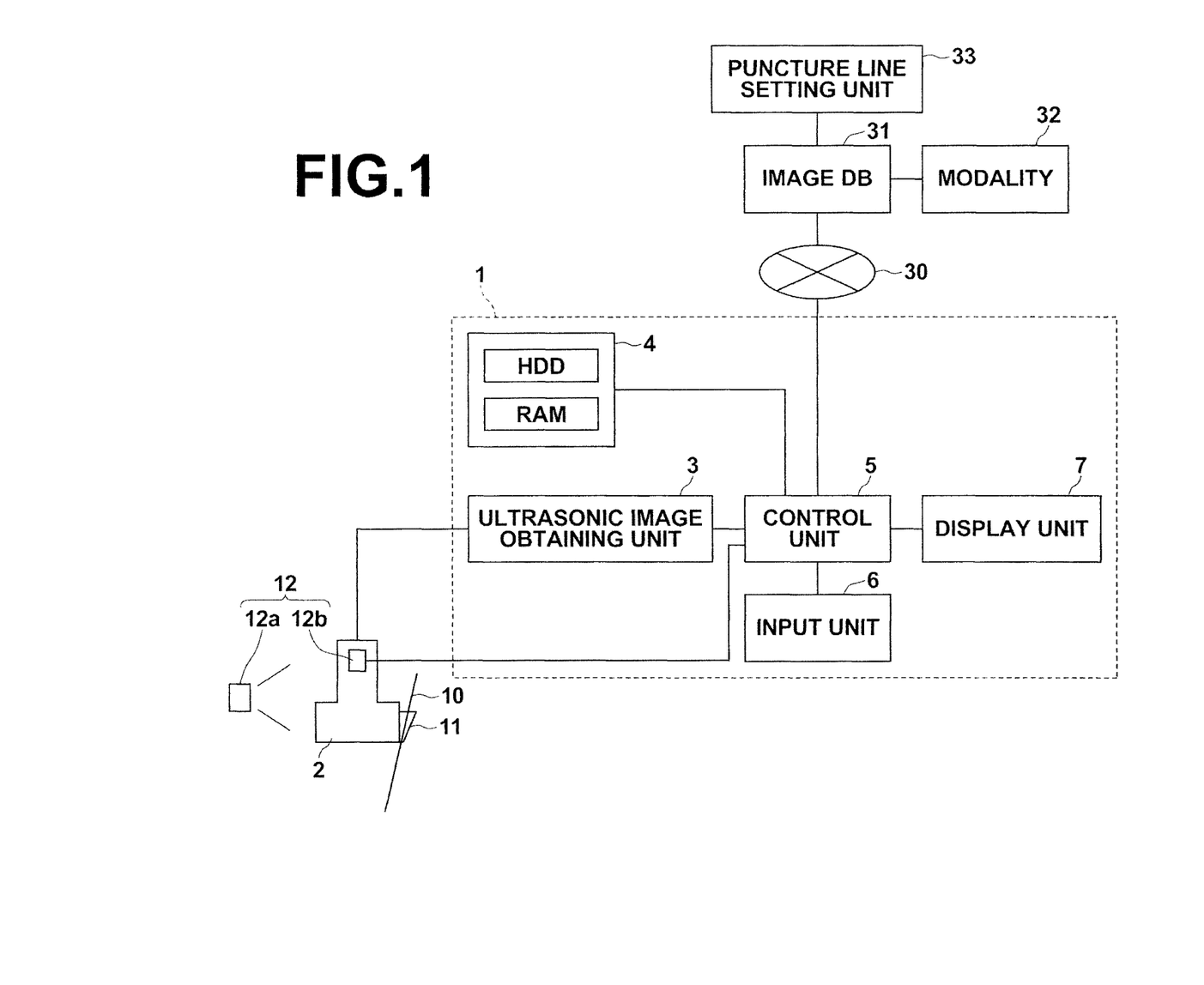
FIG. 1 is a schematic block diagram of an ultrasonic diagnostic system to which a medical image display apparatus according to a first embodiment of the present invention is applied, illustrating a configuration thereof.

FIG. 1 is a schematic block diagram of an ultrasonic diagnostic system to which a medical image display apparatus according to a first embodiment of the present invention is applied, illustrating a configuration thereof. As illustrated in FIG. 1, the ultrasonic diagnostic system 1 according to the first embodiment includes an ultrasonic probe 2, an ultrasonic image obtaining unit 3, a storage unit 4, a control unit 5, an input unit 6, and a display unit 7. Note that the ultrasonic image obtaining unit 3 and the control unit 5 constitute the medical image display apparatus of the present invention.

The ultrasonic probe 2 transmits ultrasonic waves toward a diagnostic region of a subject and receives ultrasonic waves reflected at the inside the body of the subject. The ultrasonic probe 2 of the present embodiment includes a plurality of ultrasonic transducers, which forms a one-dimensional ultrasonic transducer array, and is configured to transmit ultrasonic waves from the ultrasonic transducers to the subject and to output echo signals by receiving ultrasonic waves reflected from the subject. Note that the ultrasonic probe 2 includes a puncture adapter 11 for attaching and guiding a puncture needle 10 for puncturing the subject. In the present embodiment, a position detection unit 12 that detects a position and a direction of the ultrasonic probe 2 is provided. For example, the position detection unit 12 is constituted by a magnetism generator 12a and a magnetism sensor 12b attached to the ultrasonic probe 2, Note that the position detection unit 12 is not limited to this, and may be an optical sensor, a camera, and the like.

While driving the ultrasonic probe 2, the ultrasonic image obtaining unit 3 receives echo signals outputted from the ultrasonic probe 2, then performs various types of image processing, such as amplification, A/D conversion, and the like, on the echo signals, and generates a B-mode image (image in which the amplitude of received signals are represented by brightness (luminance) of points), as an ultrasonic image G1.

The storage unit 4 is constituted by a various types of storage media, such as a hard disk drive (HDD), a RAM, a cache memory (not shown), and the like. The HDD is a large capacity storage medium, and includes image data of a three-dimensional image V0, to be described later, and a program for realizing the processing of the control unit 5, and the like. The RAM serves as a work area when the program is executed by the control unit 5.

Here, the ultrasonic diagnostic system 1 according to the present embodiment is connected to an image database 31 via a network 30. The image database 31 includes image data of a three-dimensional image V0 obtained by imaging a subject in a modality 32, such as multi-slice CT equipment, MRI equipment, or the like. In the present embodiment, the modality 32 is assumed to be multi-slice CT equipment.

Here, the three-dimensional image V0 is obtained by stacking two-dimensional tomographic images of an abdominal region to be diagnosed obtained in order along a direction perpendicular to the tomographic surfaces and in the present embodiment, the image is generated by superimposing a plurality of tomographic images captured in the modality 32. Note that a three-dimensional image obtained using CT equipment is data in which an amount of X-ray absorption is stored in each voxel (i.e., pixel position) that forms a lattice point in a three-dimensional space, and data in which one signal value (a value that indicates the amount of X-ray absorption, in case that the image was captured by CT equipment) is given to each pixel position.

Note that, in the present embodiment, a puncture line for supporting puncturing by the puncture needle 10 is set in advance in the three-dimensional image V0. The puncture line is set by a puncture line setting unit 33. For example, the puncture line setting unit 33 is a computer provided in a doctor's terminal and a puncture line is set by executing a program for setting a puncture line on the computer.

Figure 2:
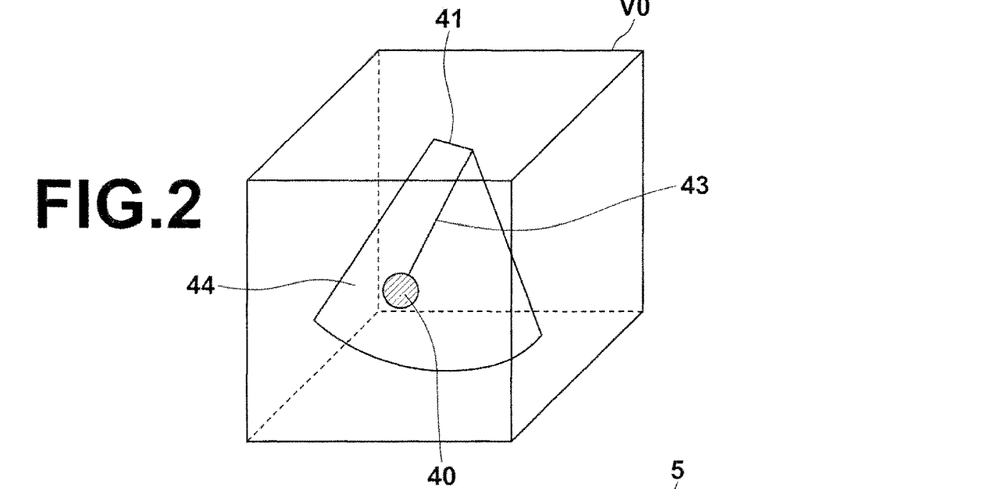
FIG. 2 illustrates the setting of a puncture line.

FIG. 2 illustrates the setting of a puncture line. A two-dimensional projection image of a virtual scan plane in a three-dimensional image V0 is displayed first on a monitor of the computer. The virtual scan plane corresponds to a scan plane when a body surface of a subject included in the three-dimensional V0 is scanned by a virtual ultrasonic probe. Note that the scan plane may be moved to any position and direction in the space of the three-dimensional image V0. This operation is performed using an input unit of the computer, such as a keyboard, a mouse, or the like. The operator identifies a lesion area 40 to be the puncture target while moving the scan plane within the three-dimensional image V0. Then, a scan plane 44 that allows the puncture needle to be approached to the lesion area 40 most safely from a body surface 41 of the subject is identified, and a straight line connecting the body surface 41 and the lesion area 40 on the scan plane 44 is set as a puncture line 43 along which the puncture needle 10 is to be inserted. Information of the coordinates of the start point and the end point of the puncture line 43 is stored in the image database 31 related to the three-dimensional image V0. Note that the scan plane 44 on which the puncture line 43 is present here will be referred to as the puncture cross-section 44 in the following description.

Figure 3:
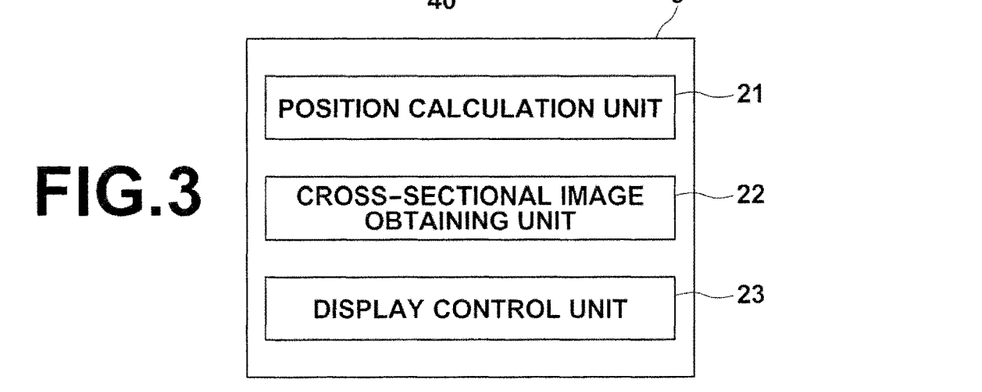
FIG. 3 is a schematic block diagram of the control unit, illustrating a configuration thereof.

The control unit 5 controls various types of processing performed by the ultrasonic diagnostic system according to the present embodiment. FIG. 3 is a schematic block diagram of the control unit 5, illustrating a configuration thereof. As illustrated in FIG. 3, the control unit 5 includes a position calculation unit 21, a cross-sectional image obtaining unit 22, and a display control unit 23. The control unit 5 is a processing unit, such as a CPU or the like, and executes the functions of the position calculation unit 21, the cross-sectional image obtaining unit 22, and the display control unit 23 by reading out the programs stored in the HDD of the storage unit 4.

The position calculation unit 21 is connected to the position detection unit 12. The position detection unit 12 is constituted by the magnetism generator 12a and the magnetism sensor 12b attached to the ultrasonic probe 2, as described above, and magnetism generated from the magnetism generator 12a is detected by the magnetism sensor 12b. Based on the detection signal, the position calculation unit 21 calculates a position and a direction of the ultrasonic probe 2 in a three-dimensional space coordinate system with its origin at the magnetism generator 12a. Then, based on the position and the direction of the ultrasonic probe 2, the position calculation unit 21 calculates position information in a three-dimensional space coordinate system with its origin at the magnetism generator 12a in the ultrasonic image G1 (hereinafter, the coordinate system of the ultrasonic image G1). In this case, the position calculation unit 21 calculates position information for each pixel of the ultrasonic image G1.

Based on the position information of the ultrasonic image G1, the cross-sectional image obtaining unit 22 identifies a cross-section of the three-dimensional image V0 stored in the storage unit 4 corresponding to the scan plane of the ultrasonic image G1 and generates a cross-sectional image G2 of the cross-section from the three-dimensional image V0. In this case, the cross-sectional image obtaining unit 22 identifies the cross-section of the three-dimensional image V0 corresponding to the scan plane of the ultrasonic image G1 by performing coordinate transform between the coordinate system of the ultrasonic image G1 and the coordinate system of the three-dimensional image V0. Hence, in the present embodiment, position alignment between the coordinate system of the ultrasonic image G1 and the coordinate system of the three-dimensional image V0 is performed. The position alignment will be described later.

Figure 4:
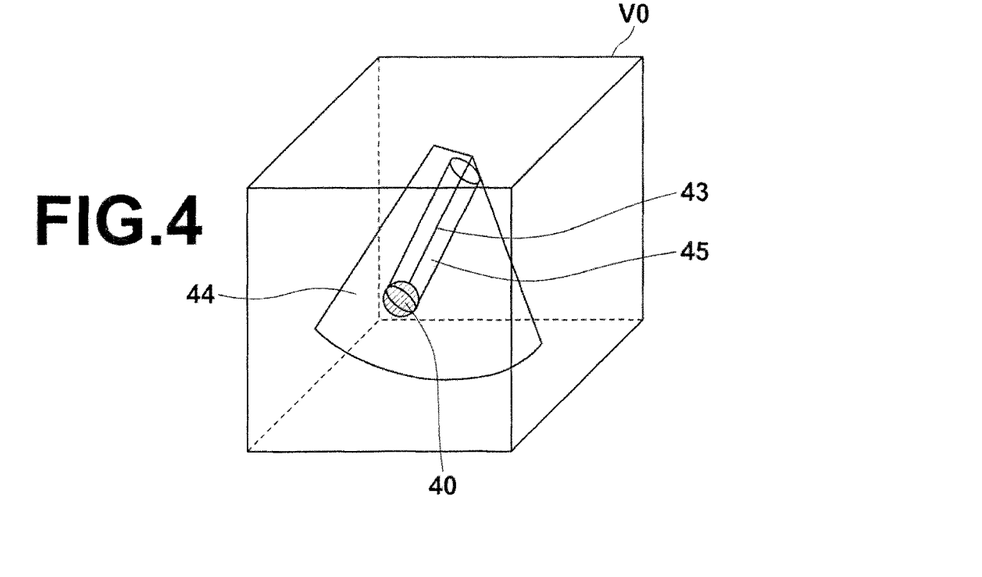
FIG. 4 illustrates the superimposition of an index.
Figure 5:
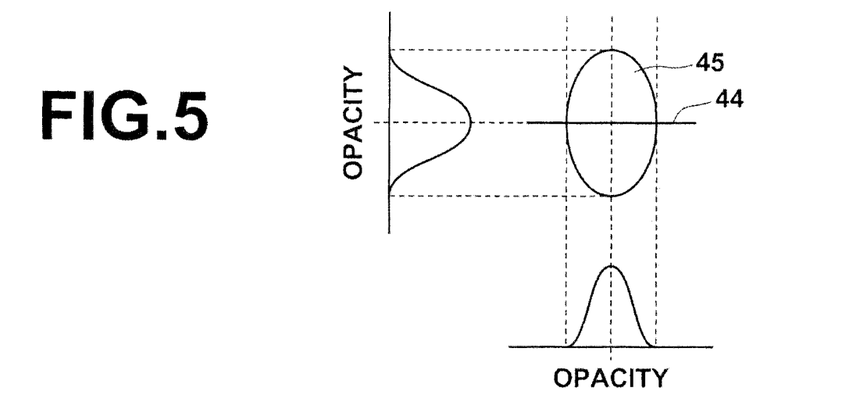
FIG. 5 illustrates opacity of the index.

The display control unit 23 superimposes an index on the three-dimensional image V0. FIG. 4 illustrates the superimposition of an index. As illustrated in FIG. 4, the index 45 is a three-dimensional columnar figure with an elliptical bottom surface, and the display control unit 23 adjusts the length and the position of the index 45 such that the vertical line passing through the center of gravity on the bottom surface is aligned with the puncture line 43 and the start point of the puncture line 43 is located on the upper surface while the end point is located on the bottom surface, and superimposes the index 45 on the three-dimensional image V0. Here, image data representing the index 45 are stored in the storage unit 4. As illustrated in FIG. 5, the index 45 is superimposed on the three-dimensional image V0 such that the short axis of the bottom surface corresponds to the puncture cross-section 44 while the long axis intersects perpendicularly with the puncture cross-section 44. Further, the index 45 may have any color, and the opacity of the color is reduced with the distance from the central axis line, i.e., from the puncture line 43, as illustrated in FIG. 5. More specifically, the opacity is reduced in a Gaussian distribution with the distance from the central axis line. Note that the opacity may be reduced linearly. The cross-sectional image obtaining unit 22 generates a cross-sectional image G2 from the three-dimensional image V0 with the index 45 superimposed thereon in the manner described above. Then, the display control unit 23 displays the ultrasonic image G1 and the cross-sectional image G2 side-by-side on the display unit 7.

The input unit 6 is constituted by a known input device, such as a keyboard, a mouse, a touch panel, and the like.

The display unit 7 is constituted by a known display device, such as a liquid crystal monitor, a CRT, or the like.

Figure 6:
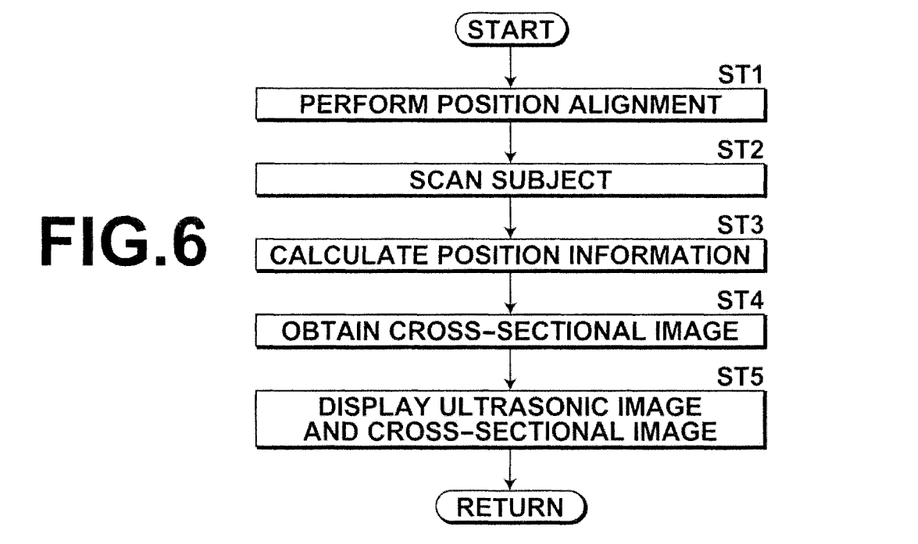
FIG. 6 is a flowchart illustrating processing steps performed in the first embodiment.

Next, processing performed in the first embodiment will be described. FIG. 6 is a flowchart illustrating processing steps performed in the first embodiment. In the first embodiment, a cross-sectional image G2 corresponding to a scan plane of an ultrasonic image G1 to be changed in real time is obtained from a three-dimensional image, and the ultrasonic image G1 and the cross-sectional image G2 are displayed side-by-side on the display unit 7. For this purpose, position alignment between the coordinate system of the ultrasonic image G1 and the coordinate system of the three-dimensional image V0 is performed first (step ST1). It is assumed that the index 45 has been superimposed on the three-dimensional image V0 by the display control unit 23.

In the position alignment, the operator displays an ultrasonic image G1 of an arbitrary scan plane by scanning a subject with the ultrasonic probe 2. Further, the operator displays a cross-sectional image G2 of an arbitrary cross-section of the three-dimensional image V0 on the display unit 7 by operating the input unit 6. Then, while comparing between the ultrasonic image G1 and the cross-sectional image G2, the operator moves at least either one of the scan plane by the ultrasonic probe 2 and the cross-section of the three-dimensional image V0 to align the scan plane by the ultrasonic probe 2 with the cross-section of the three-dimensional image V0, and displays the ultrasonic image G1 and the cross-sectional image G2 of the same cross-section of the subject on the display unit 7.

When the ultrasonic image G1 and the cross-sectional image G2 of the same cross-section of the subject is displayed, the operator issues an instruction from the input unit 6 to the control unit 5, indicating that the display of the same cross-section has been made. This causes the correspondence relationship between the coordinate system of the ultrasonic image G1 and the coordinate system of the three-dimensional image V0 to be calculated and stored in the storage unit 4, whereby the position alignment is completed. By referring to the correspondence relationship, the transformation from the coordinate system of the ultrasonic image G1 to the coordinate system of the three-dimensional image V0 may be made.

Figure 7:
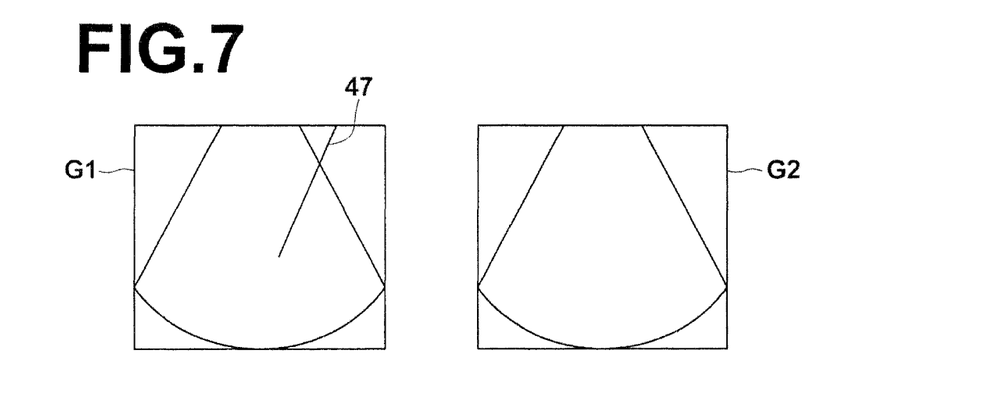
FIG. 7 illustrates an ultrasonic image and a cross-sectional image of a cross-section which is the same as that of the ultrasonic image shown on the display unit.

After the position alignment is completed, the operator scans the subject with the ultrasonic probe 2 (step ST2). Each time the scan is made, a signal indicating the position and the direction of the ultrasonic probe 2 is inputted to the position calculation unit 21 by the position detection unit 12, and the position calculation unit 21 calculates position information for each pixel of the ultrasonic image G1 (step ST3). Then, the cross-sectional image obtaining unit 22 transforms the position information of each pixel of the ultrasonic image G1 into the coordinate system of the three-dimensional image V0 with reference to the correspondence relationship stored in the storage unit 4, then based on this, identifies a cross section corresponding to the scan plane of the ultrasonic image G1, and obtains a cross-sectional image G2 of the cross-section (step ST4). Then, the display control unit 23 displays the ultrasonic image G1 and the cross-sectional image G2 on the display unit 7 (step ST5) and the processing returns to the step ST2, This causes the cross-sectional image G2 of the same cross-section as that of the ultrasonic image G1 to be displayed on the display unit 7 in a manner following the ultrasonic image G1 displayed in real time, as illustrated in FIG. 7. Note that a guide line 47 of the puncture needle 10 guided by the puncture adapter 11 is displayed in the ultrasonic image G1.

Here, in the present embodiment, the index 45 is superimposed on the three-dimensional image V0. Because the opacity of the index 45 is reduced with the distance from the central axis line, in case that the scan plane of the ultrasonic image G1 is away from the puncture cross-section 44 in which the puncture line 43 is set more than the diameter of the index 45, the index 45 is not displayed on the cross-sectional image G2, but as the scan plane of the ultrasonic image G1 comes closer the puncture cross-section, the index 45 is gradually displayed in the cross-sectional image G2.

Figure 8:
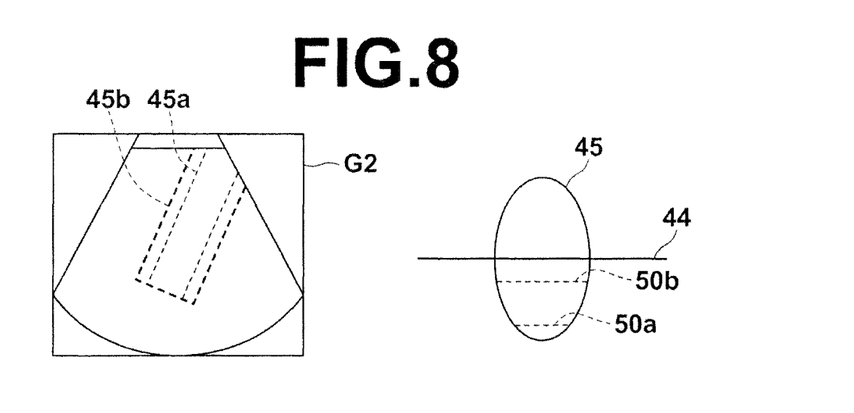
FIG. 8 illustrates a cross-sectional image on which an index is displayed in a case in which a scan plane of an ultrasonic image and a cross-section in which a puncture line is set are in parallel.

FIG. 8 illustrates the cross-sectional image G2 on which the index 45 is displayed in a case in which the scan plane of the ultrasonic image G1 and the puncture cross-section 44 are in parallel. As illustrated in FIG. 8, when the scan plane of the ultrasonic image G1, i.e. the cross-section of the cross-sectional image G2 to be displayed reaches a position 50a adjacent to an end portion of the long axis of the index 45, a thin and pale colored index 45a is displayed on the cross-sectional image G2. Then, in case that the scan plane of the ultrasonic image G1 is moved closer to the puncture cross-section 44 while maintaining the direction of the ultrasonic probe 2 in this state, the index 45 gradually becomes thicker and the color of an area adjacent to the central axis becomes darker. That is, as illustrated in FIG. 8, when the scan plane of the ultrasonic image G1 reaches a position 50b adjacent to the central axis line of the index 45, an index 45b which is thicker than the index 45a with a dark color adjacent to the central axis is displayed on the cross-sectional image G2. Then, when the scan plane of the ultrasonic image G1 and the puncture cross-section 44 are aligned, the index 45 becomes the thickest and the color adjacent to the central axis line becomes the darkest.

Figure 9:
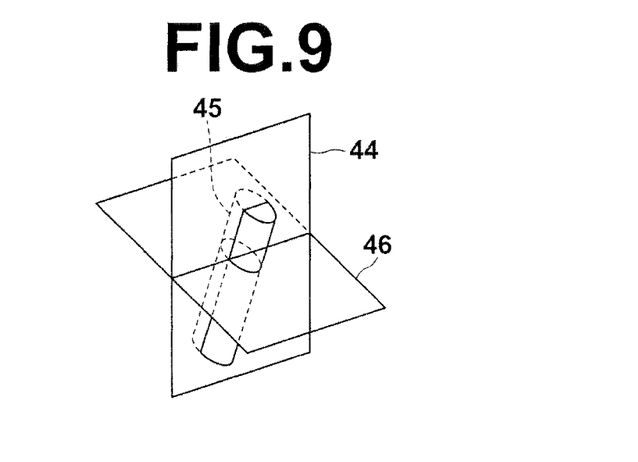
FIG. 9 illustrates a state in which a scan plane of an ultrasonic image is inclined with respect to a cross-section in which a puncture line is set.
Figure 10:
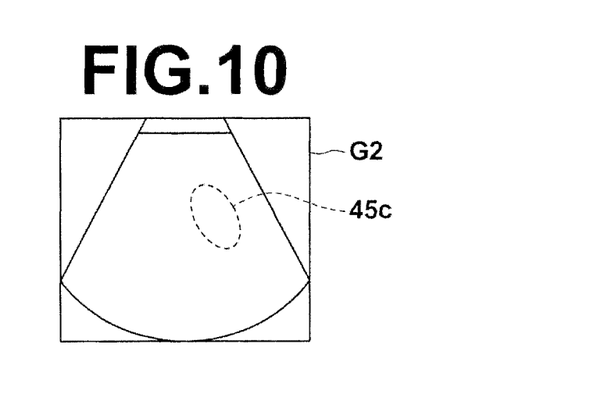
FIG. 10 illustrates a state in which an index cut by a scan plane is displayed on a cross-sectional image.

In case that the scan plane 46 is inclined with respect to the puncture cross-section 44, as illustrated in FIG. 9, the index 45 is cut by the scan plane 46 and an index 45c cut by the scan plane 46 is displayed on the cross-sectional image G2, as illustrated in FIG. 10.

Figure 11:
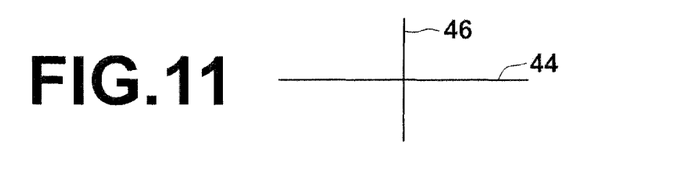
FIG. 11 illustrates a state in which a scan plane is orthogonal to a puncture cross-section.
Figure 12:
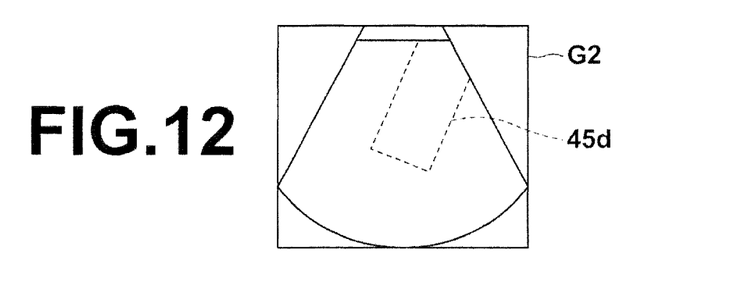
FIG. 12 illustrates a state in which a thick index is displayed on a cross-sectional image.
Figure 13:
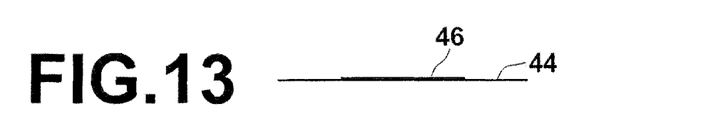
FIG. 13 illustrates a state in which a scan plane is roughly aligned with a puncture cross-section.
Figure 14:
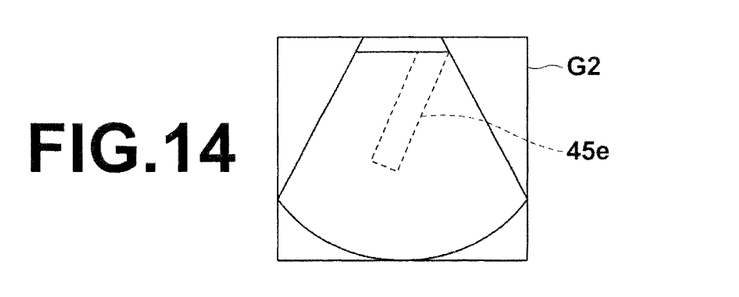
FIG. 14 illustrates a state in which a thin index is displayed on a cross-sectional image.

The index 45 according to the present embodiment is given to the three-dimensional image V0 such that the short axis of the bottom surface corresponds to the puncture cross-section 44 while the long axis intersects perpendicularly with the puncture cross-section 44. Therefore, in case that the scan plane 46 is orthogonal to the puncture cross-section 44, as illustrated in FIG. 11, a thick index 45d is displayed on the cross-sectional image G2, as illustrated in FIG. 12. In the meantime, in case that the scan plane 46 is aligned roughly with the puncture cross-section 44, as illustrated in FIG. 13, a thin index 45e is displayed on the cross-sectional image G2, as illustrated in FIG. 14.

Therefore, the operator changes the direction of the ultrasonic probe 2 such that a columnar index 45 is displayed. Then, the operator translates the ultrasonic probe 2 such that the index 45 displayed on the cross-sectional image G2 becomes the thickest and the color of the central axis line becomes the darkest. Then, the operator rotates the ultrasonic probe 2 such that the index 45 displayed on the cross-sectional image G2 becomes the thinnest, and further aligns the puncture guide line 47 with the central axis of the index 45, whereby the scan plane 46 of the ultrasonic image G1 may be aligned with the puncture cross-section 44.

By penetrating the puncture needle 10 into the subject under this state, the puncture needle 10 may be penetrated safely into the subject along the puncture line 43.

In the first embodiment, the index 45 is superimposed on the three-dimensional image V0 by the display control unit 23, display or non-display of the index 45 in the cross-sectional image G2 may be switched by an operator instruction from the input unit 6. In this case, an arrangement may be adopted in which not only display or non-display of the index 45, but also translucent display, switching between display and translucent display, or switching between non-display and translucent display is allowed. When puncturing, this allows the index 45 to be displayed translucently or hidden, so that the position of the lesion to be the puncture target in the cross-sectional image G2 may be confirmed accurately. Further, in case that the index 45 is hindering while moving the ultrasonic probe 2, the index 45 may be switched to non-display or translucent display.

In this way, in the present embodiment, the columnar index 45 having the central axis line on the puncture line 43 and opacity which is reduced with the distance from the central axis line is superimposed on the three-dimensional image V0, and the ultrasonic image G1 and the cross-sectional image G2 of the cross-section of the three-dimensional image V0 superimposed with the index 45 corresponding to the ultrasonic image G1 are displayed. Therefore, in case that the scan plane by the ultrasonic probe 2 is away from the puncture line 43, the index 45 appears thin and pale, and the index 45 becomes thicker and an area adjacent to the central axis becomes darker as the scan plane comes closer to the puncture line 43. Thus, the distance between the scan plane 46 by the ultrasonic probe 2 and the puncture cross-section 44 may be intuitively recognized by the thickness and opacity of the index 45. Further, in case that the scan plane 46 by the ultrasonic probe 2 is inclined with respect to the puncture cross-section 44, a cross-section of the index 45 appears, whereby it can also be recognized easily that the scan plane 46 by the ultrasonic probe 2 is inclined with respect to the puncture cross-section 44. Therefore, the operation of aligning the scan plane 46 by the ultrasonic probe 2 with the puncture cross-section 44 that includes the puncture line 43 may be facilitated.

Further, as the opacity of the index 45 is reduced with the distance from the central axis line, it is easier to recognize that the scan plane by the ultrasonic probe 2 comes closer to the puncture line 43.

Further, by making the index 45 to have different distance scales between a direction parallel to the puncture cross-section 44 that includes the puncture line 43 and a direction orthogonal to the puncture cross-section 44, e.g., forming the bottom surface of the index 45 in an elliptical shape, the difference in the amount of rotation and direction between the puncture cross-section 44 and the scan plane 46 by the ultrasonic probe 2 may be recognized as the difference in thickness of the index 45. Hence, the relationship in the amount of rotation and direction between the scan plane 46 and the puncture cross-section 44 may also be recognized intuitively.

Figure 15:
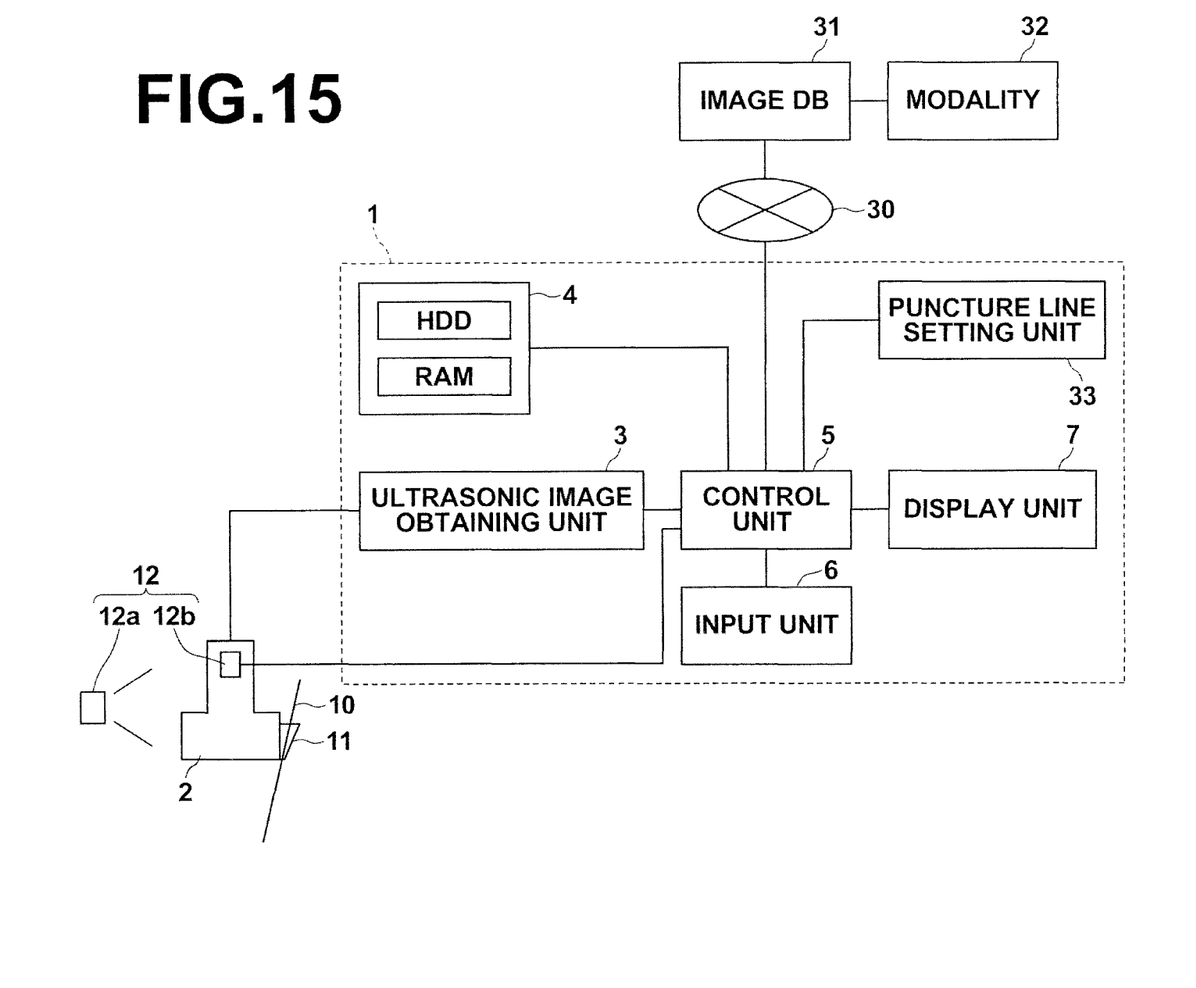
FIG. 15 is a schematic block diagram of an ultrasonic diagnostic system to which a medical image display apparatus according to a second embodiment of the present invention is applied, illustrating a configuration thereof.

In the first embodiment described above, the puncture line setting unit 33 may be provided in the ultrasonic diagnostic system 1, as illustrated in FIG. 15. Hereinafter, processing performed in this case will be described as a second embodiment.

In the second embodiment, a three-dimensional image V0 captured in the modality 32 is stored in the image database 31 without setting a puncture line 32. The ultrasonic diagnostic system 1 obtains the three-dimensional image V0 stored in the image database 31 and stores in the storage unit 4. Then, the puncture line setting unit 33 sets a puncture line 43 to the three-dimensional image V0 in response to an instruction from the input unit 7, as in the first embodiment. In this case, a two-dimensional projection image of the three-dimensional image V0 is displayed on the display unit 7, and the operator sets a puncture line 43 to the three-dimensional image V0 by operating the input unit 6. In the second embodiment, the puncture line setting unit 33 stores the coordinate positions of the start and end points of the set puncture line 43 in the storage unit 4.

When the puncture line 43 is set by the puncture line setting unit 33, an index 45 is superimposed on the three-dimensional image V0 with the puncture line 43 set thereto based on the coordinate positions of the start and end points of the puncture line 43, as in the first embodiment described above. Then, by changing the position and the direction of the ultrasonic probe 2, the index 45 may be displayed on the cross-sectional image G2, as in the first embodiment.

In the first embodiment described above, an arrangement may be adopted in which the index 45 is superimposed on the three-dimensional image V0 in the puncture line setting unit 33. In this case, as the three-dimensional image V0 superimposed with the index 45 is obtained in the ultrasonic diagnostic system 1, non-display, translucent display, and the like of the index 45 on the cross-sectional image G2 cannot be performed. Therefore, in case that the index 45 is superimposed on the three-dimensional image V0 in the puncture line setting unit 33, it is preferable that both the three-dimensional image V0 superimposed with the index 45 and the three-dimensional image V0 before the index 45 is superimposed are stored in the image database 31, and both of the three-dimensional images V0 are obtained in the ultrasonic diagnostic system 1. This allows switching between display and non-display of the index 45 to be made by displaying a cross-sectional image G2 of the corresponding cross-section of the three-dimensional image V0 not superimposed with the index 45 in case that the index 45 on the cross-sectional image G2 is desired to be hidden.

In the first and the second embodiments, the bottom surface of the index 45 is formed in an elliptical shape but not limited to this, and any shape may be used as long as it differs in distance scale between a direction parallel to the surface that includes the puncture line 43 and a direction orthogonal to the surface, such as a rectangle, a polygon collapsed in one direction, and the like. Here, in the embodiments described above, the index 45 is superimposed on the three-dimensional image V0 such that the long axis is orthogonal to the puncture cross-section 44, but the index 45 may be superimposed on the three-dimensional image V0 such that the short axis is orthogonal to the puncture cross-section 44. In this case, the index 45 is displayed the most thick on the cross-sectional image G2 when the scan plane 46 and the puncture cross-section 44 are aligned in the amount of rotation and direction.

Further, the bottom shape of the index is not limited to the shape that differs in distance scale between a direction parallel to the surface that includes the puncture line and a direction orthogonal to the surface, and may be a shape having the same distance scale in a direction parallel to the surface that includes the puncture line and a direction orthogonal to the surface by forming the bottom shape in a circle, a square, an equilateral triangle, a regular polygon, or the like, thereby forming the index in a circular cylindrical shape or a prism shape.

Further, in the embodiments described above, the opacity of the index 45 is reduced with the distance from the central axis line, but the index 45 may be made completely opaque.

What is claimed is:

1. A medical image display apparatus, comprising:
   at least one hardware processor configured to implement:
      controlling scanning of a subject with an ultrasonic probe and obtaining an ultrasonic image of the subject;
      obtaining a cross-sectional image of a cross-section of a three-dimensional image corresponding to the ultrasonic image from the three-dimensional image, the three-dimensional image including a puncture line set for a puncture needle and a superimposed columnar index having a central axis line on the puncture line and opacity which is reduced with the distance from the central axis line; and
      controlling a display to display the cross-sectional image,
   wherein the three-dimensional image comprises a modality other than ultrasound,
   wherein the central axis line of the superimposed columnar index is superimposed on a central axis of the puncture line, and
   wherein, in a cross-section through the superimposed columnar index and perpendicular to each of the central axis line and the central axis, the superimposed columnar index comprises an elliptical periphery and the opacity is linearly reduced with the distance from the central axis line to the elliptical periphery.

2. The medical image display apparatus as claimed in claim 1, wherein the opacity of the index is reduced linearly with the distance from the central axis line.

3. The medical image display apparatus as claimed in claim 1, wherein the opacity of the index is reduced in a Gaussian distribution with the distance from the central axis line.

4. The medical image display apparatus as claimed in claim 1, wherein the index has different distance scales in a direction parallel to a puncture cross-section that includes the puncture line and a direction orthogonal to the puncture cross-section.

5. The medical image display apparatus as claimed in claim 1, wherein the index has a circular cylindrical shape.

6. The medical image display apparatus as claimed in claim 1, wherein the index is written in the three-dimensional image.

7. The medical image display apparatus as claimed in claim 1, wherein the index is generated separately from the three-dimensional image, and the at least one hardware processor is further configured to superimpose the index on the three-dimensional image and obtains the cross-sectional image.

8. The medical image display apparatus as claimed in claim 7, wherein the at least one hardware processor is further configured to control the display to switch between at least two of display, non-display, and translucent display of the index on the cross-sectional image.

9. The medical image display apparatus as claimed in claim 1, wherein the at least one hardware processor is further configured to set the puncture line in the three-dimensional image.

10. A medical image display method, comprising the steps of:
    scanning a subject with an ultrasonic probe and obtaining an ultrasonic image of the subject;
    obtaining a cross-sectional image of a cross-section of a three-dimensional image corresponding to the ultrasonic image from the three-dimensional image, the three-dimensional image including a puncture line set for a puncture needle and a superimposed columnar index having a central axis line on the puncture line and opacity which is reduced with the distance from the central axis line; and
    displaying the cross-sectional image,
    wherein the three-dimensional image comprises a modality other than ultrasound,
    wherein the central axis line of the superimposed columnar index is superimposed on a central axis of the puncture line, and
    wherein, in a cross-section through the superimposed columnar index and perpendicular to each of the central axis line and the central axis, the superimposed columnar index comprises an elliptical periphery and the opacity is linearly reduced with the distance from the central axis line to the elliptical periphery.

11. A non-transitory computer-readable recording medium containing a medical image display program that causes a computer to perform the steps of:
    scanning a subject with an ultrasonic probe and obtaining an ultrasonic image of the subject;
    obtaining a cross-sectional image of a cross-section of a three-dimensional image corresponding to the ultrasonic image from the three-dimensional image, the three-dimensional image including a puncture line set for a puncture needle and a superimposed columnar index having a central axis line on the puncture line and opacity which is reduced with the distance from the central axis line; and
    displaying the cross-sectional image, wherein the three-dimensional image comprises a modality other than ultrasound, wherein the central axis line of the superimposed columnar index is superimposed on a central axis of the puncture line, and wherein, in a cross-section through the superimposed columnar index and perpendicular to each of the central axis line and the central axis, the superimposed columnar index comprises an elliptical periphery and the opacity is linearly reduced with the distance from the central axis line to the elliptical periphery.

12. The medical image display apparatus according to claim 1, wherein, in the cross-section and in the cross-sectional image, the superimposed columnar index is wider than the puncture line.

13. The medical image display apparatus according to claim 1, wherein the at least one hardware processor is further configured to obtain the cross-section image by identifying the cross-sectional image by performing a coordinate transform between a first coordinate system of the ultrasonic image and a second coordinate system of the three-dimensional image, and wherein the three-dimensional image comprises voxels.

14. The medical image display apparatus according to claim 1, wherein the at least one hardware processor is further configured to control the display to display the cross-section of the three-dimensional image to be displayed at a same time as the ultrasonic image is displayed by the display with the puncture line displayed on the ultrasonic image.

* * * * *